United States Patent
Kim et al.

(10) Patent No.: US 10,811,197 B2
(45) Date of Patent: Oct. 20, 2020

(54) HYDROTHERMALLY GROWN BATIO$_3$, SRTIO$_3$, AND BA$_x$SR$_{1-x}$TIO$_3$ ON TIO$_2$ NANOTUBE LAYERS FOR ULTRA-HIGH CHARGE DENSITY CAPACITORS

(71) Applicants: University of Florida Research Foundation, Inc., Gainesville, FL (US); KOREA ELECTRONICS TECHNOLOGY INSTITUTE, Gyeonggi-do (KR)

(72) Inventors: Kyoung Tae Kim, Gainesville, FL (US); Yong-Kyu Yoon, Gainesville, FL (US); Dongsu Kim, Gyeonggi-do (KR)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 148 days.

(21) Appl. No.: 16/064,611

(22) PCT Filed: Dec. 21, 2016

(86) PCT No.: PCT/US2016/067965
§ 371 (c)(1),
(2) Date: Jun. 21, 2018

(87) PCT Pub. No.: WO2017/112742
PCT Pub. Date: Jun. 29, 2017

(65) Prior Publication Data
US 2018/0374660 A1   Dec. 27, 2018

Related U.S. Application Data

(60) Provisional application No. 62/270,190, filed on Dec. 21, 2015.

(51) Int. Cl.
*H01G 11/46*   (2013.01)
*C25D 11/26*   (2006.01)
(Continued)

(52) U.S. Cl.
CPC ............ *H01G 11/46* (2013.01); *A61L 2/16* (2013.01); *B32B 3/10* (2013.01); *C25D 11/26* (2013.01);
(Continued)

(58) Field of Classification Search
CPC .......... H01G 11/46; H01G 9/04; H01G 9/042; H01G 9/048; H01G 11/86; A61L 2/16; B32B 3/10; C25D 11/26; Y02E 60/13
See application file for complete search history.

(56) References Cited

U.S. PATENT DOCUMENTS 7,147,834 B2   12/2006   Wong et al.
9,023,186 B1 *   5/2015   Patibandla ............. C25D 5/022
                                                                         205/124

(Continued)

FOREIGN PATENT DOCUMENTS

CN   102060325 B   10/2012

OTHER PUBLICATIONS

International Search Report in co-pending, related PCT Application No. PCT/US2016/067965.

(Continued)

*Primary Examiner* — Michael P McFadden
(74) *Attorney, Agent, or Firm* — Thomas Horstemeyer, LLP

(57) ABSTRACT

Various examples are provided for hydrothermally grown BaTiO$_3$, SrTiO$_3$, and Ba$_x$Sr$_{1-x}$TiO$_3$ on TiO$_2$ nanotube layers, which can be used in ultra-high charge density capacitors. In one example, a method includes forming a first anodized titanium oxide (ATO) layer on a layer of titanium by anodization, the first ATO layer having a nanotubular morphology; removing the first ATO layer from the layer of titanium; forming a second ATO layer having a nanotubular morphology on the layer of titanium by anodization; and (Continued)

hydrothermally growing a layer of $MTiO_3$ on a surface of the second ATO layer, where M is Ba, Sr, or $Ba_xSr_{1-x}$. In another example, an ultra-high density charge capacitor includes a first electrode layer; an ATO layer disposed on the first electrode layer; a layer of $MTiO_3$ on a surface of the ATO layer; and a second electrode layer disposed on the layer of $MTiO_3$.

20 Claims, 5 Drawing Sheets

(51) Int. Cl.
  *H01G 9/048* (2006.01)
  *A61L 2/16* (2006.01)
  *B32B 3/10* (2006.01)
  *H01G 9/042* (2006.01)
  *H01G 9/04* (2006.01)
  *H01G 11/86* (2013.01)

(52) U.S. Cl.
  CPC ............. *H01G 9/04* (2013.01); *H01G 9/042* (2013.01); *H01G 9/048* (2013.01); *H01G 11/86* (2013.01); *Y02E 60/13* (2013.01)

(56) References Cited

U.S. PATENT DOCUMENTS

| | | | |
|---|---|---|---|
| 2005/0111162 A1 | 5/2005 | Osaka et al. | |
| 2007/0232017 A1* | 10/2007 | Baniecki | H01G 4/085 438/396 |
| 2009/0090411 A1 | 4/2009 | Choi et al. | |
| 2010/0320089 A1* | 12/2010 | Misra | C01G 45/00 205/109 |
| 2013/0003254 A1 | 1/2013 | Koutsaroff et al. | |

OTHER PUBLICATIONS

Yang Yang, Xiaohui Wang, Changku Sun and Longtu Li, "Structure study of single crystal BaTiO3 nanotube arrays produced by the hydrothermal method", Nanotechnology vol. 20, 055709 (5pp), Feb. 2009.

Upendra A. Joshi and Jae Sung Lee, "Template-Free Hydrothermal Synthesis of Single-Crystalline Barium Titanate and Strontium Titanate Nanowires", Small vol. 1, Issue 12, pp. 1172-1176, Dec. 2005.

Jin Yang, Jie Zhang, Chongyun Liang, Min Wang, Pengfei Zhao, Mengmei Liu, Jiwei Liu, and Renchao Che, "Ultrathin BaTiO3 Nanowires with High Aspect Ratio: A Simple One-Step Hydrothermal Synthesis and Their Strong Microwave Absorption", ACS Appl. Mater. Interfaces, vol. 5, pp. 7146-7151, Jul. 2013.

Zhao Deng, Ying Dai, Wen Chen, Xinmei Pei, Jihong Liao, "Synthesis and Characterization of Bowl-Like Single-Crystalline BaTiO3 Nanoparticles", Nanoscale Res Lett vol. 5, pp. 1217-1221, May 2010.

Roozeboom, F. et al., "High-value MOS capacitor arrays in ultradeep trenches in silicon", Microelectron. Eng. vol. 53, pp. 581-584, Jun. 2000.

* cited by examiner

| | 1st anodization | 2nd anodization |
|---|---|---|
| Morphology | Nanotubular | Hexagonal |
| Pore diameter | ~120nm | ~90nm |
| Wall thickness | ~20nm | ~20nm |

HYDROTHERMALLY GROWN BATIO$_3$, SRTIO$_3$, AND BA$_x$SR$_{1-x}$TIO$_3$ ON TIO$_2$ NANOTUBE LAYERS FOR ULTRA-HIGH CHARGE DENSITY CAPACITORS

CROSS REFERENCE TO RELATED APPLICATIONS

This application is the 35 U.S.C. § 371 national stage application of PCT Application No. PCT/US2016/067965, filed Dec. 21, 2016, which claims priority to, and the benefit of, U.S. provisional application entitled "Hydrothermally Grown BaTiO$_3$, SrTiO$_3$, and Ba$_x$Sr$_{1-x}$TiO$_3$ on TiO$_2$ Nanotube Layers for Ultra-High Charge Density Capacitors" having Ser. No. 62/270,190, filed Dec. 21, 2015, where both of these applications are hereby incorporated by reference in their entireties.

BACKGROUND

Supercapacitors or ultracapacitors are electrochemical capacitors with high energy densities, which offer energy storage that can be several orders of magnitude greater than conventional capacitor technologies. These capacitors offer low temperature performance with minimal effect on efficiency and fast charge and discharge capabilities without damage.

SUMMARY

Embodiments of the present disclosure are related to hydrothermally grown BaTiO$_3$, SrTiO$_3$, and Ba$_x$Sr$_{1-x}$TiO$_3$ on TiO$_2$ nanotube layers, which can be used in ultra-high charge density capacitors.

In one embodiment, among others, a method comprises forming a first anodized titanium oxide (ATO) layer on a layer of titanium by anodization, the first ATO layer having a nanotubular morphology; removing the first ATO layer from the layer of titanium; forming a second ATO layer on the layer of titanium by anodization, the second ATO layer having a nanotubular morphology; and hydrothermally growing a layer of MTiO$_3$ on a surface of the second ATO layer, where M is Ba, Sr, or Ba$_x$Sr$_{1-x}$. In one or more aspects of these embodiments, x can be in a range from about 0.1 to about 0.9, or can be in a range from about 0.5 to about 0.8. The method can comprise disposing an electrode layer on the layer of MTiO$_3$. The electrode layer can comprise platinum, titanium nitride (TiN) or tantalum nitride (TaN).

In one or more aspects of these embodiments, the layer of titanium can be a titanium foil. The method can comprise disposing the layer of titanium on a substrate. The method can comprise preparing a surface on the layer of titanium by polishing before forming the first ATO layer. The surface on the layer of titanium can be mechanically polished. The nanotubular morphology can be hexagonal. In one or more aspects of these embodiments, forming the second ATO layer can comprise low temperature thermal annealing.

In another embodiment, an ultra-high density charge capacitor comprises a first electrode layer; an anodized titanium oxide (ATO) layer disposed on the first electrode layer, the first ATO layer having a nanotubular morphology; a layer of MTiO$_3$ on a surface of the ATO layer, where M is Ba, Sr, or Ba$_x$Sr$_{1-x}$; and a second electrode layer disposed on the layer of MTiO$_3$. In one or more aspects of these embodiments, the ATO layer can comprise ATO nanotubes that are perpendicularly aligned with the first electrode layer. The layer of MTiO$_3$ can be on an inner surface of the ATO nanotubes. The second electrode layer can fill an inner portion of the ATO nanotubes.

In one or more aspects of these embodiments, the electrode layer can comprise platinum, titanium nitride (TiN) or tantalum nitride (TaN). The first electrode layer can comprise titanium (Ti) and/or platinum (Pt). The first electrode layer can be disposed on a substrate. The substrate can comprise a layer of silicon dioxide (SiO$_2$) adjacent to the first electrode layer. In one or more aspects of these embodiments, x can be in a range from about 0.1 to about 0.9, or can be in a range from about 0.5 to about 0.8.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
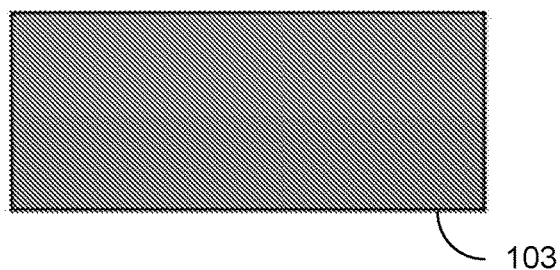
FIGS. 1A through 1F illustrating an example of a fabrication process for a nanotubular morphology used in a nanoporous supercapacitor in accordance with various embodiments of the present disclosure.

Disclosed herein are various embodiments related to ultra-high charge density capacitors. For example, $BaTiO_3$ (BTO), $SrTiO_3$ (STO), and $Ba_xSr_{1-x}TiO_3$ (BST) can be hydrothermally grown on $TiO_2$ nanotube layers to produce ultra-high charge density capacitors. Reference will now be made in detail to the description of the embodiments as illustrated in the drawings, wherein like reference numbers indicate like parts throughout the several views.

Figure 1D:
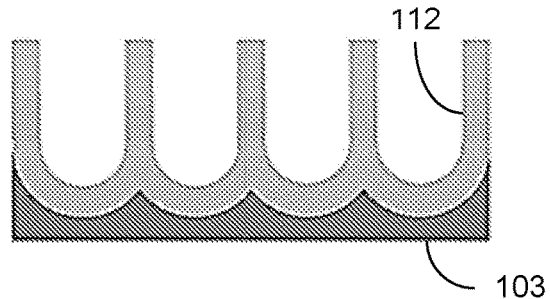
Figure 1B:
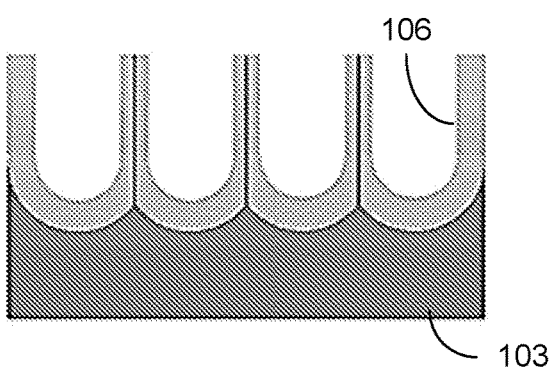
Figure 1E:
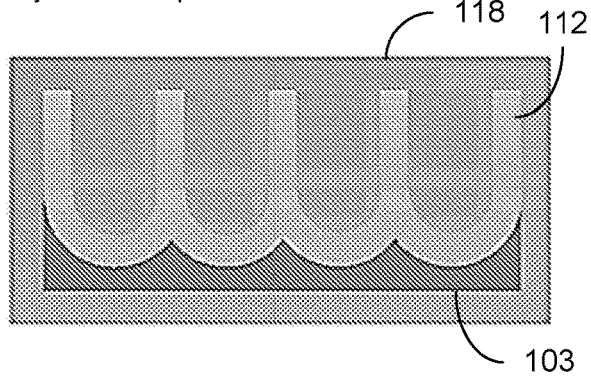
Figure 1C:
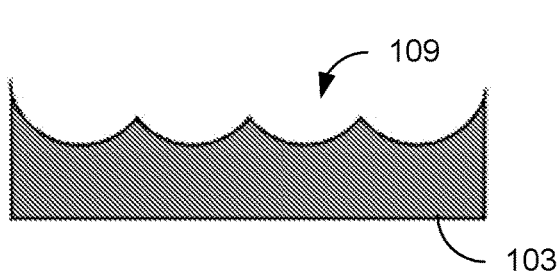
Figure 1F:
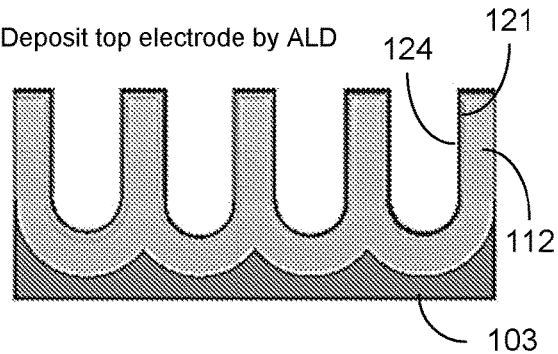
Figure 2:
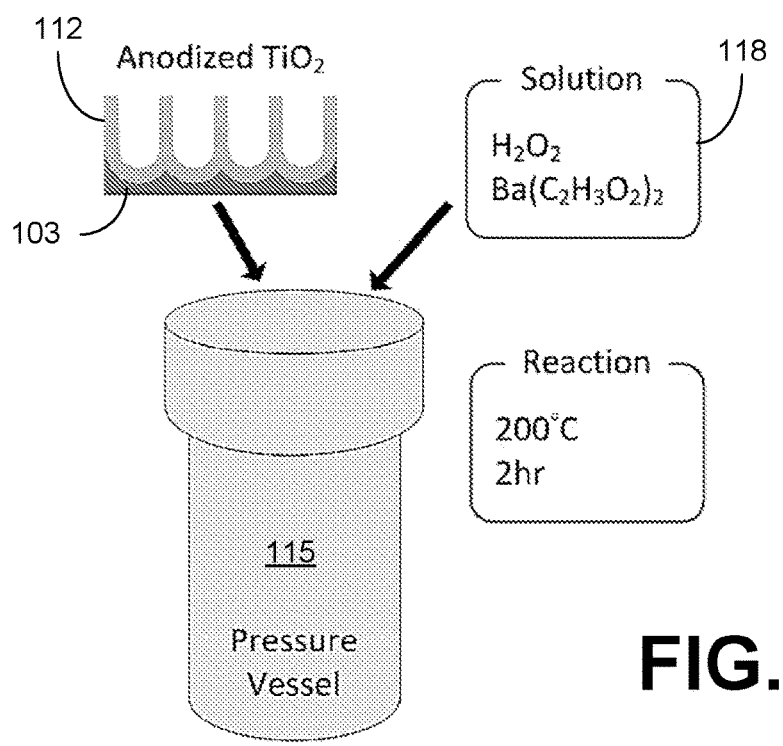
FIG. 2 illustrates an example of a hydrothermal process used in the fabrication process of FIG. 1E in accordance with various embodiments of the present disclosure.

Referring to FIGS. 1A through 1F, shown is a graphical representation illustrating an example of a fabrication process for a nanoporous supercapacitor based on high-K dielectric materials (e.g., $MTiO_3$, where M can be Ba, Sr, or $Ba_xSr_{1-x}$). Beginning with FIG. 1A, titanium (Ti) foil 103 can be mechanically polished to obtain a smooth and uniform surface. In other implementations, a Ti layer can be formed by deposition. In FIG. 1B, the Ti foil 103 is anodized at, e.g., 60V for 6 hours to generate anodized titanium oxide (ATO) 106 with nanotubular morphology. Since the mechanical polishing only yields a roughness of a few microns, the first ATO layer 106 still has a non-uniform morphology. At FIG. 1C, 1M of hydrochloric acid (HCl) solution can be used to strip away the first ATO layer 106, leaving a periodic honeycomb-like dimple nanopattern 109 on the surface of the Ti foil 103. This nanopattern 109 serves as the guideline to the second anodization for the honeycomb-like (hexagonal) nanotubular ATO 112 with enhanced uniformity, as shown in FIG. 1D. Low temperature thermal annealing can be performed at, e.g., 400° C. to transfer rutile $TiO_2$ to anatase stage $TiO_3$, which is electrically conductive and serves as a bottom electrode of the fabricated supercapacitor. In FIG. 1E, a hydrothermal process can be carried out in an autoclave 115 with an aqueous solution 118 containing barium acetate, strontium acetate, and/or sodium hydroxide. FIG. 2 schematically illustrates the hydrothermal process can be carried out in the autoclave 115. The anatase stage ATO of FIG. 1D is immersed in the solution 118, and then pressurized and heated at, e.g., 200° C. for 2 hours. An ion transfer mechanism occurs, which transforms the surface of the ATO 112 to barium strontium titanate (BST) 121 (or BTO or STO based on the composition of the solution 118). Finally, a metal layer 124 is deposited on top of the BST layer 121 to form a nanopore based high charge density supercapacitor as shown in FIG. 1F.

Figure 3A:
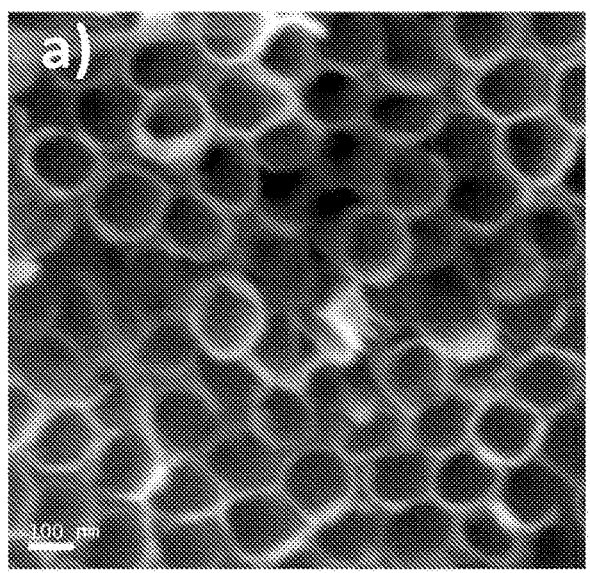
FIGS. 3A and 3B are scanning electron microscope (SEM) images of a first anodized titanium oxide (ATO) layer and a second ATO layer of the fabrication process of FIGS. 1B and 1D, respectively, in accordance with various embodiments of the present disclosure.
Figure 3B:
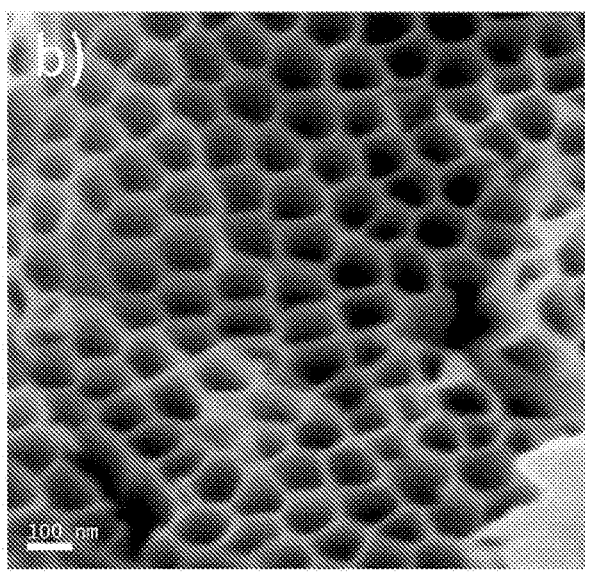
Figures 4, 5:
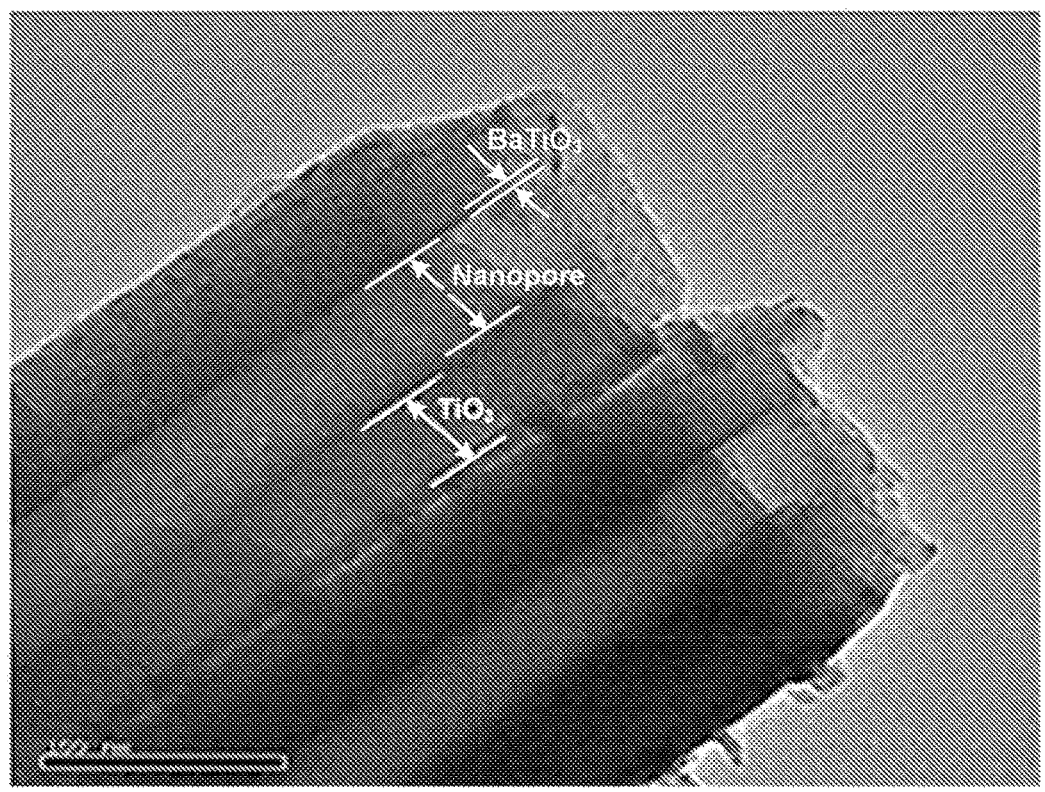
FIG. 4 is a table showing the morphology and dimensions of the first and second ATO layers of FIGS. 3A and 3B in accordance with various embodiments of the present disclosure.
FIG. 5 is a transmission electron microscope (TEM) image of the second ATO with BaTiO$_3$ (BTO) formed on the surface by the hydrothermal process of FIG. 2 in accordance with various embodiments of the present disclosure.

Referring to FIGS. 3A and 3B, shown are scanning electron microscope (SEM) images of the first nanotubular ATO layer 106 and the second hexagonal nanotubular ATO layer 112, respectively. The nanostructure can be analyzed with an image analysis tool such as, e.g., ImageJ to determine the structure dimensions. The table in FIG. 4 illustrates an example of the morphology and dimensions of the ATO 106 and 112 after the first and second anodization processes of FIGS. 1B and 1D, respectively. The nanopore diameter shrinks from 120 nm to 90 nm with the same wall thickness as can be seen in FIGS. 3A and 3B.

FIG. 5 shows a transmission electron microscope (TEM) image of the second ATO 112 with $BaTiO_3$ (BTO) formed on the surface by the hydrothermal process of FIG. 2. A BTO thickness of 5 nm and the uniform conversion of the interfacial layer were observed.

Figure 6:
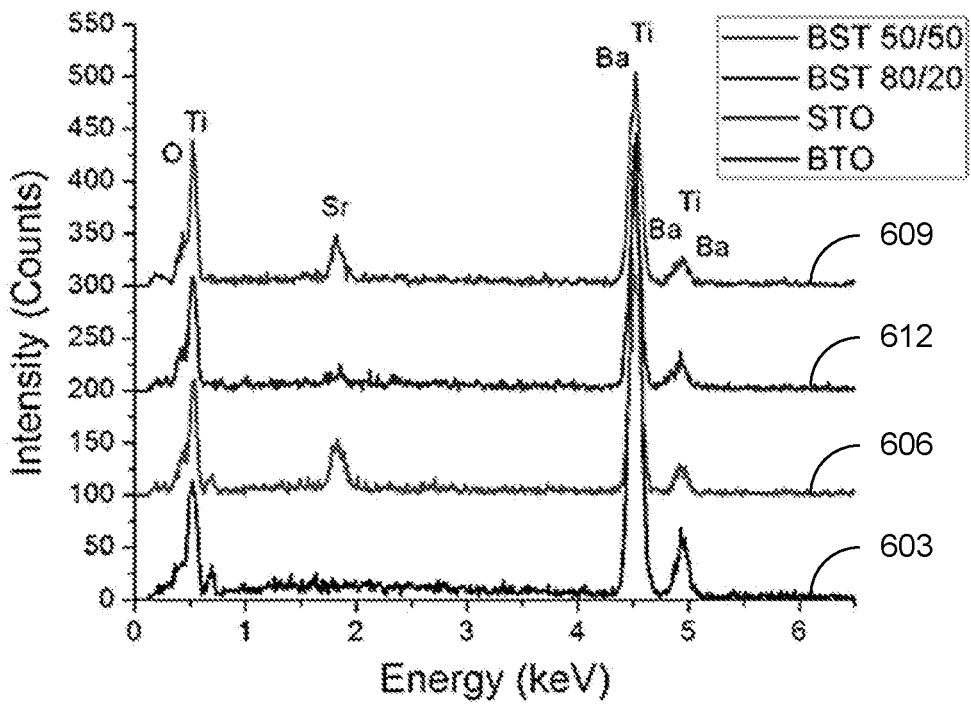
FIG. 6 illustrates energy dispersive X-ray spectroscope measurements of different concentrations of Ba and Sr in accordance with various embodiments of the present disclosure.
Figure 7:
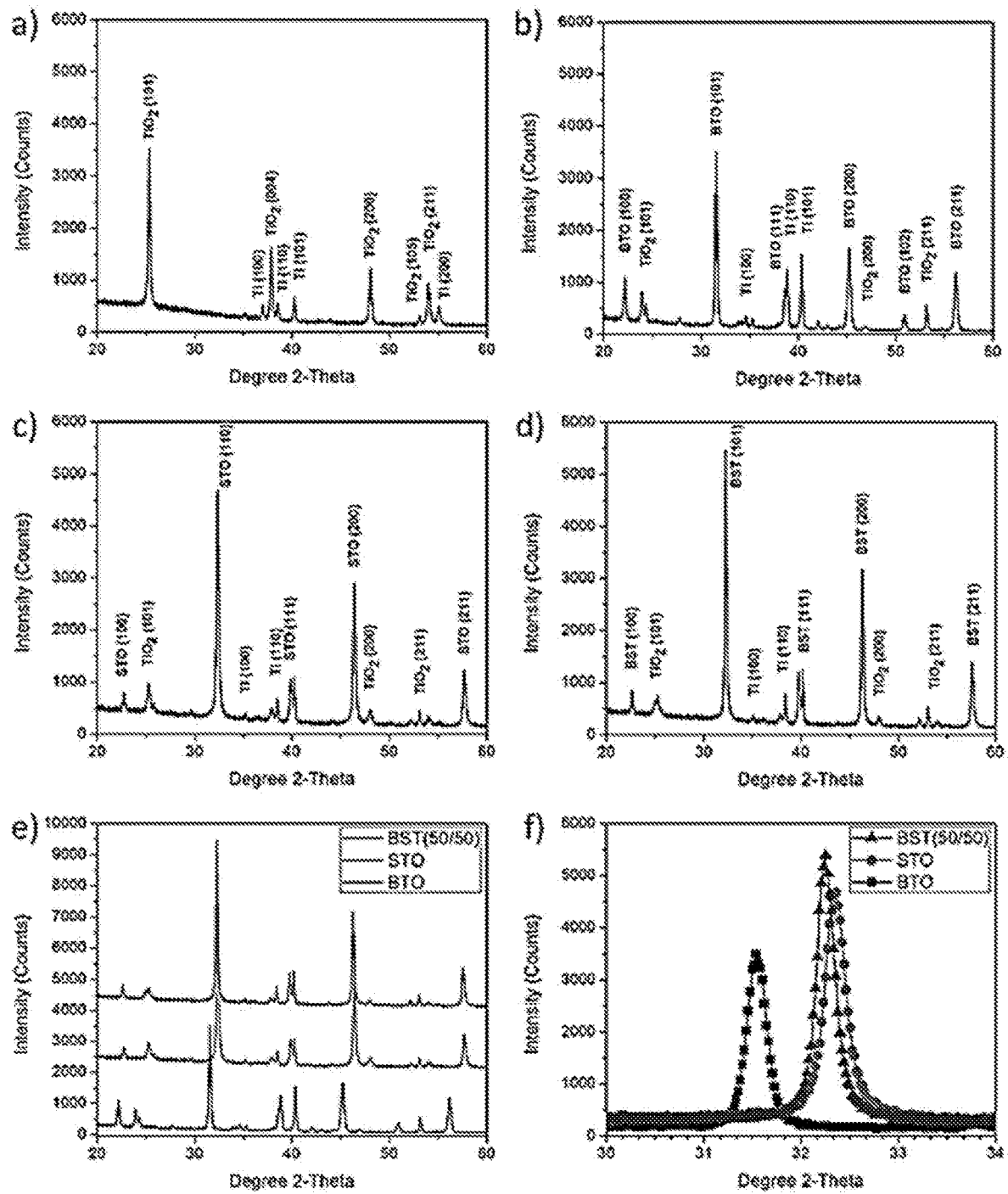
FIG. 7 illustrates X-ray diffraction (XRD) measurements of different concentrations of Ba and Sr in accordance with various embodiments of the present disclosure.

FIG. 6 shows the energy dispersive X-ray spectroscope (EDX) of $BaTiO_3$ (plo5 603), $SrTiO_3$ (plot 606), $Ba_{0.5}Sr_{0.5}TiO_3$ (plot 609), and $Ba_{0.8}Sr_{0.2}TiO_3$ (plot 612). X-ray diffraction (XRD) can be used to examine the crystallinity of the $MTiO_3$. FIG. 7 illustrates the XRD measurement results on (a) anatase $TiO_2$, (b) $BaTiO_3$ (BTO), (c) $SrTiO_3$ (STO), (d) $Ba_{0.5}Sr_{0.5}TiO_3$ (BST 50/50), as well as (e) combined and (f) high resolution plots of the $TiO_3$ (101) peaks. FIG. 7(a) shows the anatase stage ATO before the hydrothermal process. FIGS. 7(b), 7(c) and 7(d) show the well crystallized $Ba_xSr_{1-x}TiO_3$ with the different values for x of 1, 0, and 0.5, respectively. The value of x can in a range from about 0.1 to about 0.9, a range from about 0.5 to about 0.9, a range from about 0.5 to about 0.8 or smaller ranges as can be appreciated. Both the EDX and the XRD show that ATO can be successfully converted to BST by the hydrothermal process.

Figure 8:
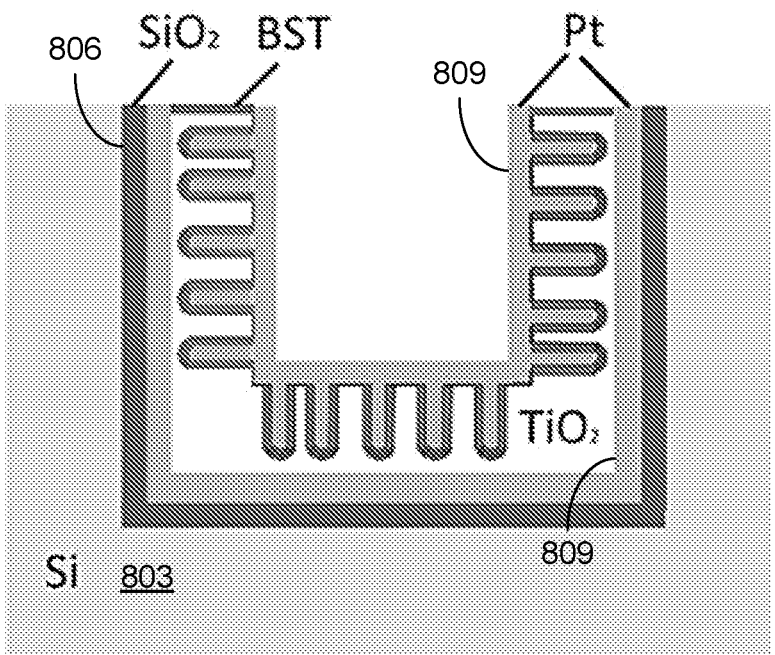
FIG. 8 is a schematic representation of a hybrid supercapacitor fabricated with the nanoporous morphology illustrated in FIGS. 1A through 1F in accordance with various embodiments of the present disclosure.

A hybrid supercapacitor can be provided with both micro and nanoporous morphology using the fabrication process described above. FIG. 8 illustrates an example of the hybrid supercapacitor. A silicon (Si) substrate 803 can be designed and patterned using, e.g., deep reactive-ion-etching (DRIE) to form a microscale trench. Silicon dioxide ($SiO_2$) 806, platinum (Pt) 809, and/or titanium (Ti) can be deposited by DC sputtering or atomic layer deposition. The Pt and/or Ti layer can then be anodized to realize the nanoporous morphology, followed by the hydrothermal process. The hybrid supercapacitor with integrated micro/nanoporocity can increase the surface to volume ratio significantly, which enhances the capacitance density of the device.

Disclosed is an ultra-high charge density capacitor that exhibits a capacitance density of 200 $nF/mm^2$ or more with a high breakdown voltage by using a hydrothermally grown $MTiO_3/TiO_2$ nanotube array (where M can be Ba, Sr, or $Ba_xSr_{1-x}$) on a deposited electrode. In order to enhance the capacitance value, a high aspect ratio nanoporous architecture and a high dielectric constant thin film are used. A high aspect ratio $TiO_2$ nanotube array can be formed by two-step anodization of Ti as discussed above. The high dielectric BTO/STO/BST can be hydrothermally grown on the $TiO_2$ layer. The thickness can be controlled by the time of the hydrothermal process. The thin film is conformally formed along the cylindrical or hexagonal nanotubes that are perpendicularly aligned to the Ti layer or film. The high aspect ratio BTO/STO/BST nanotube thin films lead to a much higher area which is proportional to the $TiO_2$ nanotube layer thickness, resulting in enhancement of the capacitance density compared to a planar or trench structure based capacitor. The nanotube length of the $TiO_2$ nanotube array can be controlled by anodization time. Part of the $TiO_2$ nanotube array is transformed into thin film BTO/STO/BST after the hydrothermal treatment, followed by the electrode (e.g., TiN or Pt) deposited for conformal coating on the BTO/STO/BST layer.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method, comprising:
forming a first anodized titanium oxide (ATO) layer on a layer of titanium by anodization, the first ATO layer having a nanotubular morphology;
removing the first ATO layer from the layer of titanium;
forming a second ATO layer on the layer of titanium by anodization, the second ATO layer having a nanotubular morphology; and
hydrothermally growing a layer of $MTiO_3$ on a surface of the second ATO layer, where M is Ba, Sr, or $Ba_xSr_{1-x}$.

2. The method of claim 1, wherein x is in a range from about 0.1 to about 0.9.

3. The method of claim 2, wherein x is in a range from about 0.5 to about 0.8.

4. The method of claim 1, comprising disposing an electrode layer on the layer of $MTiO_3$.

5. The method of claim 4, wherein the electrode layer comprises platinum, titanium nitride (TiN) or tantalum nitride (TaN).

6. The method of claim 1, wherein the layer of titanium is a titanium foil.

7. The method of claim 1, comprising disposing the layer of titanium on a substrate.

8. The method of claim 1, comprising preparing a surface on the layer of titanium by polishing before forming the first ATO layer.

9. The method of claim 8, wherein the surface on the layer of titanium is mechanically polished.

10. The method of claim 1, wherein the nanotubular morphology is hexagonal.

11. The method of claim 1, wherein forming the second ATO layer comprises low temperature thermal annealing.

12. An ultra-high density charge capacitor, comprising:
a first electrode layer;
an anodized titanium oxide (ATO) layer disposed on the first electrode layer, the first ATO layer having a nanotubular morphology;
a layer of $MTiO_3$ on a surface of the ATO layer, where M is Ba, Sr, or $Ba_xSr_{1-x}$; and
a second electrode layer disposed on the layer of $MTiO_3$.

13. The ultra-high density charge capacitor of claim 12, wherein the ATO layer comprises ATO nanotubes that are perpendicularly aligned with the first electrode layer.

14. The ultra-high density charge capacitor of claim 13, wherein the layer of $MTiO_3$ is on an inner surface of the ATO nanotubes.

15. The ultra-high density charge capacitor of claim 14, wherein the second electrode layer fills an inner portion of the ATO nanotubes.

16. The ultra-high density charge capacitor of claim 12, wherein the second electrode layer comprises platinum, titanium nitride (TiN) or tantalum nitride (TaN).

17. The ultra-high density charge capacitor of claim 12, wherein the first electrode layer comprises titanium (Ti).

18. The ultra-high density charge capacitor of claim 12, wherein the first electrode layer is disposed on a substrate.

19. The ultra-high density charge capacitor of claim 18, wherein the substrate comprises a layer of silicon dioxide ($SiO_2$) adjacent to the first electrode layer.

20. The ultra-high density charge capacitor of claim 12, wherein x is in a range from about 0.1 to about 0.9.

* * * * *